(12) United States Patent
Bruder et al.

(10) Patent No.: US 8,718,343 B2
(45) Date of Patent: May 6, 2014

(54) ITERATIVE RECONSTRUCTION OF CT IMAGES WITHOUT A REGULARIZATION TERM

(75) Inventors: Herbert Bruder, Höchstadt (DE);
Martin Petersilka, Adelsdorf (DE);
Rainer Raupach, Heroldsbach (DE);
Karl Schwarz, Roth (DE)

(73) Assignee: Siemens Aktiengesellschaft, Munich (DE)

( * ) Notice: Subject to any disclaimer, the term of this patent is extended or adjusted under 35 U.S.C. 154(b) by 249 days.

(21) Appl. No.: 13/111,315

(22) Filed: May 19, 2011

(65) Prior Publication Data

US 2011/0293160 A1    Dec. 1, 2011

(30) Foreign Application Priority Data

Jun. 1, 2010 (DE) .......................... 10 2010 022 305

(51) Int. Cl.
*G06K 9/00* (2006.01)
(52) U.S. Cl.
USPC .......................................................... 382/131
(58) Field of Classification Search
USPC ........ 382/128, 131; 250/363.04; 378/4, 5, 11, 378/21
See application file for complete search history.

(56) References Cited

U.S. PATENT DOCUMENTS

| | | | | |
|---|---|---|---|---|
| 8,175,359 B2 * | 5/2012 | O'Halloran et al. | ........... | 382/131 |
| 8,411,914 B1 * | 4/2013 | Mangoubi et al. | ............. | 382/128 |
| 2005/0135664 A1 * | 6/2005 | Kaufhold et al. | ............. | 382/131 |
| 2006/0171578 A1 * | 8/2006 | Novak | ........................... | 382/131 |
| 2007/0019851 A1 * | 1/2007 | Nishide et al. | ................ | 382/131 |
| 2007/0081704 A1 * | 4/2007 | Pan et al. | ....................... | 382/128 |
| 2010/0086185 A1 * | 4/2010 | Weiss | ............................ | 382/131 |
| 2010/0309198 A1 * | 12/2010 | Kauffmann | .................... | 345/419 |
| 2011/0037761 A1 * | 2/2011 | Mistretta et al. | .............. | 345/419 |
| 2011/0038517 A1 * | 2/2011 | Mistretta et al. | .............. | 382/128 |

FOREIGN PATENT DOCUMENTS

| | | |
|---|---|---|
| DE | 102005038940 A1 | 3/2007 |
| DE | 102009039987 A1 | 3/2011 |
| DE | 102010022305 | 12/2012 |

OTHER PUBLICATIONS

Sunnegardh, J. et al; Regularized iterative weighted filtered backprojection for helical cone-beam CT. Medical Physics 35, vol. 9, Sep. 2008, p. 4173-4185.; Others; 2008.
Dr. T. Flohr: RSNA2009 in Chicago in der Session Physics (CT: New Methods) am Nov. 29, 2009 von 11:15-11:25 Uhr, Vortrag; Others; 2009.
P.-E. Danielsson et al.: Combining Fourier and iterative methods in computer tomography. Analysis of an iteration scheme. The 2D-case. Report No. LiTH-ISY-R-2634, Linköping Univ., 2004, p. 1-50; Others; 2004.

(Continued)

*Primary Examiner* — Bhavesh Mehta
*Assistant Examiner* — Shervin Nakhjavan
(74) *Attorney, Agent, or Firm* — Harness, Dickey & Pierce

(57) ABSTRACT

A method is disclosed for reconstructing image data of an examination object from measured data, wherein the measured data was captured previously during a relative rotary motion between a radiation source of a computed tomography system and the examination object. In at least one embodiment, the measured data is modified to achieve a particular grayscale characteristic of the image data to be reconstructed. The image data is calculated by way of an iterative algorithm using the modified measured data, wherein no arithmetic step for reducing noise is employed in the iterations.

17 Claims, 3 Drawing Sheets

(56) References Cited

OTHER PUBLICATIONS

E. Eibenberger et al.: Edge-Preserving Denoising for Segmentation in CT-Images. Bildverarbeitung für die Medizin 2008, Informatik Aktuell, 2008, Part 13, p. 257-261, http://ftp.informatik.rwth-aachen.de/Publications/CEUR-WS/Vol-347/p257.pdf; Others; 2008.

German priority application DE 10 2010 022 305.0 filed on Jun. 1, 2010 and not yet published.

* cited by examiner

ITERATIVE RECONSTRUCTION OF CT IMAGES WITHOUT A REGULARIZATION TERM

PRIORITY STATEMENT

The present application hereby claims priority under 35 U.S.C. §119 on German patent application number DE 10 2010 022 305.0 filed Jun. 1, 2010, the entire contents of which are hereby incorporated herein by reference.

FIELD

At least one embodiment of the invention generally relates to a method for reconstructing image data of an examination object from measured data, this measured data having been captured previously during a relative rotary motion between a radiation source of a computed tomography system and the examination object.

BACKGROUND

Tomographic imaging methods are characterized in that inner structures of an examination object can be examined without the need to perform an operation on the examination object. One possible type of tomographic image generation consists in recording a number of projections of the object to be examined from different angles. A two-dimensional sectional image or a three-dimensional volume image of the examination object can be calculated from these projections.

An example of such a tomographic imaging method is computed tomography. Methods for scanning an examination object with a CT system are generally known, with use being made here for example of circular scans, sequential circular scans with feed motion or spiral scans. Other types of scans that are not based on circular motions are also possible, e.g. scans with linear segments. Using at least one x-ray source and at least one opposing detector, absorption data of the examination object is recorded from different recording angles and the absorption data or projections collected in this way are allocated by way of corresponding reconstruction methods to sectional images through the examination object.

For reconstructing computed tomography images from x-ray CT datasets of a computed tomography device (CT device), i.e. from the captured projections, what is known as Filtered Backprojection (FBP) is nowadays used as the standard method. Following data capture a so-called "rebinning" step is normally performed, in which the data generated with the fan-shaped beam emanating from the source is reordered so that it is present in a form as if the detector was being hit by x-ray beams traveling toward it in parallel. The data is then transformed into the frequency domain. Filtering takes place in the frequency domain, and the filtered data is then transformed back. With the aid of the data resorted and filtered in this way, a backprojection onto the individual voxels within the volume of interest then takes place. However, with the traditional FBP methods problems arise with so-called low-frequency cone beam artifacts and spiral artifacts as a result of the approximative way in which they work. Furthermore, in traditional FBP methods the image definition is linked to the image noise. The higher the definition achieved, the higher also the image noise and vice versa.

Hence iterative reconstruction methods have recently been developed, with which at least some of these limitations can be eliminated. In such an iterative reconstruction method initial image data is first of all reconstructed from the projection measured data. To this end, for example, a convolution backprojection method can be used. Then from this initial image data synthetic projection data is generated with a "projector", a projection operator, which should map the measuring system mathematically as closely as possible. The difference from the measured signals is then backprojected with the operator adjoining the projector and in this way a residual image is reconstructed, with which the initial image is updated. The updated image data can in turn be used in a next iteration step to generate new synthetic projection data with the aid of the projection operator, and from this again to form the difference from the measured signals and to calculate a new residual image, with which again the image data for the current iteration stage is improved, etc. Using such a method, image data can be reconstructed which has a relatively good image definition and nevertheless a low image noise. Examples of iterative reconstruction methods are the algebraic reconstruction technique (ART), the simultaneous algebraic reconstruction technique (SART), iterated filtered backprojection (IFBP), or even statistical iterative image reconstruction techniques.

SUMMARY

In at least one embodiment of the invention, a method for the iterative reconstruction of CT images is demonstrated. Furthermore, a corresponding control and arithmetic unit, a CT system, a computer program and a computer program product are also demonstrated.

Advantageous embodiments and developments constitute the subject matter of subclaims.

In at least one embodiment of the inventive method for reconstructing image data of an examination object from measured data this measured data was previously captured during a relative rotary motion between a radiation source of a computed tomography system and the examination object. The measured data is modified to obtain a particular grayscale characteristic of the image data to be reconstructed. The image data is calculated by way of an iterative algorithm using the modified measured data. No arithmetic step for reducing noise is used in the iterations.

The image data is calculated iteratively. Thus several, i.e. at least two, iterations take place, image data for the current iteration being calculated from image data for the preceding iteration in each iteration. For the zero-th iteration the image data is determined from the measured data or the modified measured data.

In the known iterative CT image reconstruction methods a so-called regularization term is employed, which for every iteration uses smoothing to remove some of the noise from the currently calculated iteration image. This arithmetic step is dispensed with in the inventive method. In other words, the algorithm for calculating the iteration image from the image data for the last iteration does not contain such a component.

The lack of noise reduction in the iterations can be at least partially redressed in that the measured data is modified and is then used to calculate the iteration images. This modification is such that the image data present after the iterative reconstruction has a particular grayscale characteristic. This grayscale characteristic corresponds to a texture or a frequency characteristic of the image data. Preferably the particular grayscale characteristic can be selected; i.e. a well-defined grayscale characteristic which the reconstructed image data possesses can be selected.

The image data to be calculated by the iterative algorithm can be two-dimensional sectional images or also three-dimensional volume images of the examination object.

In a development of at least one embodiment of the invention, a CT convolution kernel specifying the particular grayscale characteristic is employed during the modification of the measured data. As a result it can be guaranteed that image data with a well-defined texture is present at the output of the iteration loop. Such CT convolution kernels are e.g. known from conventional FBP image reconstruction. Examples are: body kernel B30, skull kernel H40. In particular the CT convolution kernel can be employed in the form of its modulation transfer function.

It is particularly advantageous if after the iterative algorithm the calculated image data undergoes noise-reduction processing. This may involve filtering the image data. The noise reduction in this case takes place, in contrast to conventional iterative calculation methods, not in each iteration, but on conclusion of the iterations.

In an embodiment of the invention the particular grayscale characteristic is adjusted to the noise-reduction processing. The reason for this is that many noise-reduction processing operations require a particular noise characteristic of the image data which is to be processed to be present; if it is not, the noise-reduction processing does not produce any satisfactory results. Thus to make the image data for the iterative reconstruction compatible with such a requirement of noise-reduction processing, the iterative reconstruction takes place such that the particular grayscale characteristic is present as an output image. This is effected by the attributes of the modified image data.

According to an embodiment of the invention the noise-reduction processing includes non-linear filtering which smoothes the image data while preserving the edges. Such a smoothing does not take place uniformly across the entire image; instead, smoothing preferably takes place in homogeneous image regions, whereas in image regions with edges smoothing is largely dispensed with. In this way the smoothing preserves the edges.

It is possible to output the image obtained by the noise-reduction processing as a result image. Alternatively, after the noise-reduction processing the image data processed in this way can be merged with the unprocessed image data. In this way even better image attributes can be obtained where appropriate.

According to an embodiment of the invention, in the case of the iterative algorithm, first image data is calculated from the original measured data, and image data for the following iterations is calculated using the modified measured data. This means that the unmodified image data is employed only to calculate the zero-th iteration image, whereas during the following iterations only the modified measured data is still employed for image calculation.

It is advantageous if in the case of the iterative algorithm measured data is calculated in each iteration from calculated image data and is compared to the modified measured data. The use of the modified measured data thus serves for comparison with synthetic, i.e. calculated, measured data. This can be effected by a simple or weighted difference calculation. The aim of the iterative algorithm is to reconstruct the image data such that measured data calculated from it matches the modified measured data as closely as possible. Correction data can then be calculated from the comparison and be used to correct the image data.

At least one embodiment of the inventive control and arithmetic unit is used for reconstructing image data for an examination object from measured data of a CT system. It includes a program memory for storing program code, whereby program code is present in it—where appropriate along with other program code—which is suitable for executing a method of the type described above or for effecting or controlling this execution. At least one embodiment of the inventive CT system includes such a control and arithmetic unit. Furthermore, it may contain other components which are required e.g. for capturing measured data.

At least one embodiment of the inventive computer program has program code which is suitable for performing the method of the type described above if the computer program is run on a computer.

At least one embodiment of the inventive computer program product includes program code stored on a computer-readable data carrier which is suitable for performing the method of the type described above if the computer program is run on a computer.

BRIEF DESCRIPTION OF THE DRAWINGS

In the following, the invention is explained in greater detail on the basis of an example embodiment. The drawings show.

DETAILED DESCRIPTION OF THE EXAMPLE EMBODIMENTS

Figure 1:
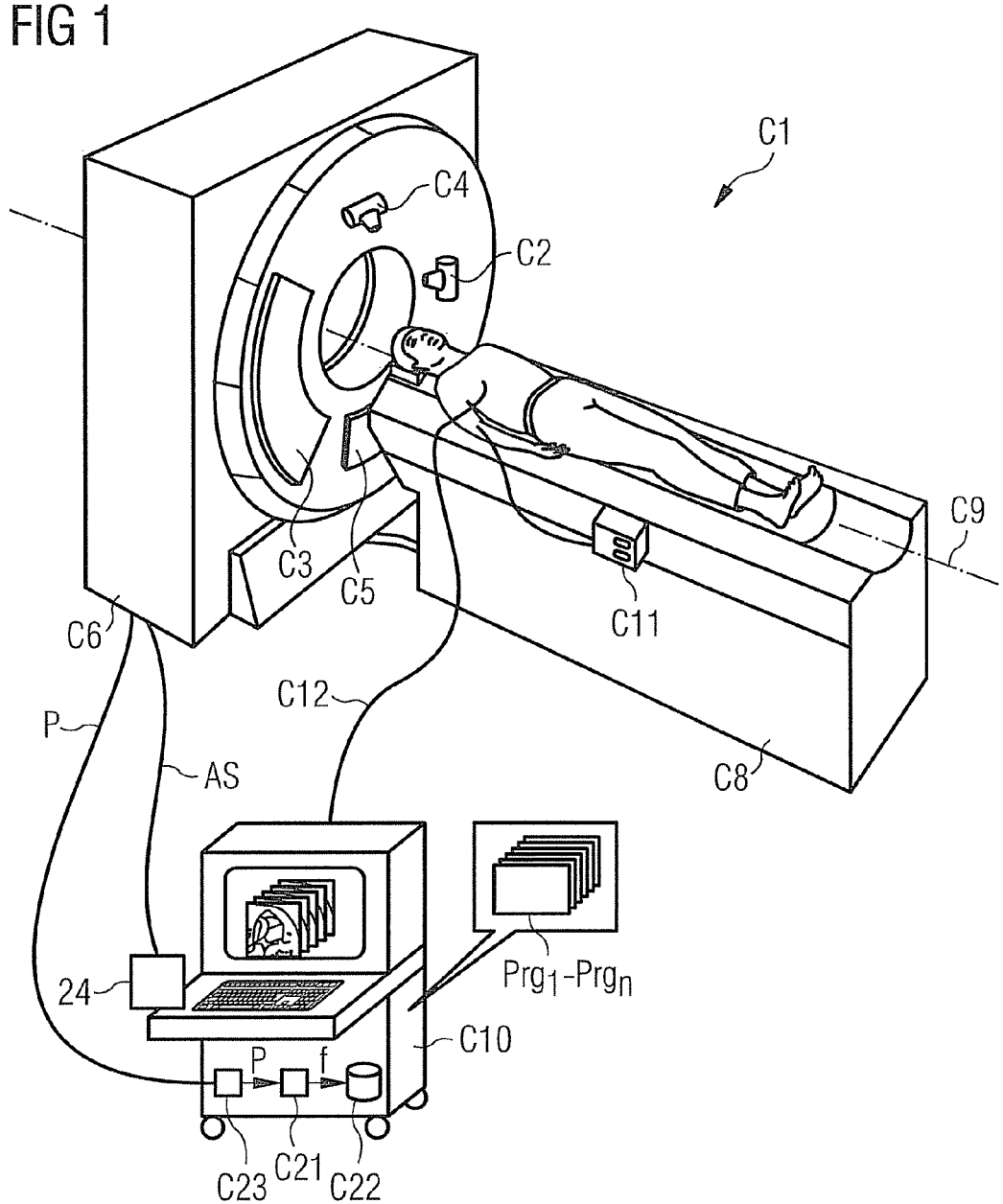
FIG. 1: a first diagrammatic illustration of an example embodiment of a computed tomography system with an image reconstruction component.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 first of all illustrates diagrammatically a first computed tomography system C1 with an image reconstruction unit C21. This is a so-called third-generation CT device, to which however the invention is not restricted. In the gantry housing C6 is a closed gantry (not shown here) on which a first x-ray tube C2 with an opposing detector C3 is arranged. Optionally in the CT system shown here a second x-ray tube C4 with an opposing detector C5 is arranged, so that thanks to the additionally available emitter/detector combination a higher time resolution can be achieved, or when using different x-ray energy spectra in the emitter/detector systems "dual-energy" examinations can also be performed.

The CT system C1 furthermore has a patient couch C8, on which a patient can be pushed into the measuring field during the examination along a system axis C9, also called the Z axis, it being possible for the scanning itself to take place solely in the examination region of interest both as a pure circular scan without the patient being fed forward. The motion of the patient couch C8 relative to the gantry is affected by a suitable motorization. During this motion the x-ray source C2 or C4 rotates around the patient in each case. In this case the detector C3 or C5 runs in parallel opposite the x-ray source C2 or C4 respectively, to capture projection measured data, which is then used for reconstructing sectional images.

Alternatively to a sequential scan, in which the patient is gradually pushed between the individual scans through the examination field, it is of course also possible to perform a spiral scan, in which the patient is continuously pushed along the system axis C9 through the examination field between x-ray tube C2 or C4 and detector C3 or C5 respectively during the rotary scanning with the x-ray radiation. Thanks to the motion of the patient along the axis C9 and the simultaneous rotation of the x-ray source C2 or C4 a helical path is produced during a spiral scan for the x-ray source C2 or C4 relative to the patient during the measurement. This path can also be achieved by pushing the gantry along the axis C9 while the patient remains stationary. Furthermore, it is possible to move the patient continuously and periodically back and forth between two points.

The CT system 10 is controlled by a control and arithmetic unit C10 with computer program code $Prg_1$ to $Prg_n$ present in a memory. It is pointed out that these computer program codes $Prg_1$ to $Prg_n$ are of course also contained on an external storage medium and if required can be loaded into the control and arithmetic unit C10.

From the control and arithmetic unit C10 acquisition control signals AS can be transmitted via a control interface 24 in order to control the CT system C1 according to particular measuring protocols. The acquisition control signals AS here relate to e.g. the x-ray tubes C2 and C4, it being possible for rules on their performance and the time points at which they are activated and deactivated to be made, as well as the gantry, it being possible for rules on its rotational speed to be made, as well as the table feed.

Since the control and arithmetic unit C10 has an input console, measurement parameters can be input by a user or operator of the CT device C1, and these then control the data capture in the form of acquisition control signals AS. Information on currently used measurement parameters can be displayed on the monitor of the control and arithmetic unit C10; in addition, further information relevant to the operator can be displayed.

The projection measured data p or raw data acquired by the detector C3 or C5 is passed via a raw data interface C23 to the control and arithmetic unit C10. This raw data p is then further processed in an image reconstruction component C21, if appropriate after suitable preprocessing. The image reconstruction component C21 is implemented in this exemplary embodiment in the control and arithmetic unit C10 in the form of software on a processor, e.g. in the form of one or more of the computer program codes $Prg_1$ to $Prg_n$. In respect of the image reconstruction it is the case, as already explained in respect of the control of the measurement operation, that the computer program codes $Prg_1$ to $Prg_n$ are also contained on an external storage medium and if required can be loaded into the control and arithmetic unit C10. Furthermore, it is possible for the control of the measurement operation and the image reconstruction to be performed by different arithmetic units.

The image data f reconstructed by the image reconstruction component C21 is then stored in a memory C22 of the control and arithmetic unit C10 and/or is output in the normal way on the monitor of the control and arithmetic unit C10. It can also be imported, via an interface not shown in FIG. 1, into a network connected to the computed tomography system C1, for example a radiological information system (RIS), and stored in a mass memory accessible there or output as images.

The control and arithmetic unit C10 can additionally also perform the function of an EKG, a line C12 being used to dissipate the EKG potentials between patient and control and arithmetic unit C10. In addition the CT system C1 shown in FIG. 1 also has a contrast agent injector C11, via which contrast agent can additionally be injected into the patient's bloodstream, so that e.g. the patient's vessels, in particular the ventricles of the beating heart, can be better displayed. This also makes it possible to perform perfusion measurements, for which the proposed method is likewise suitable.

Figure 2:
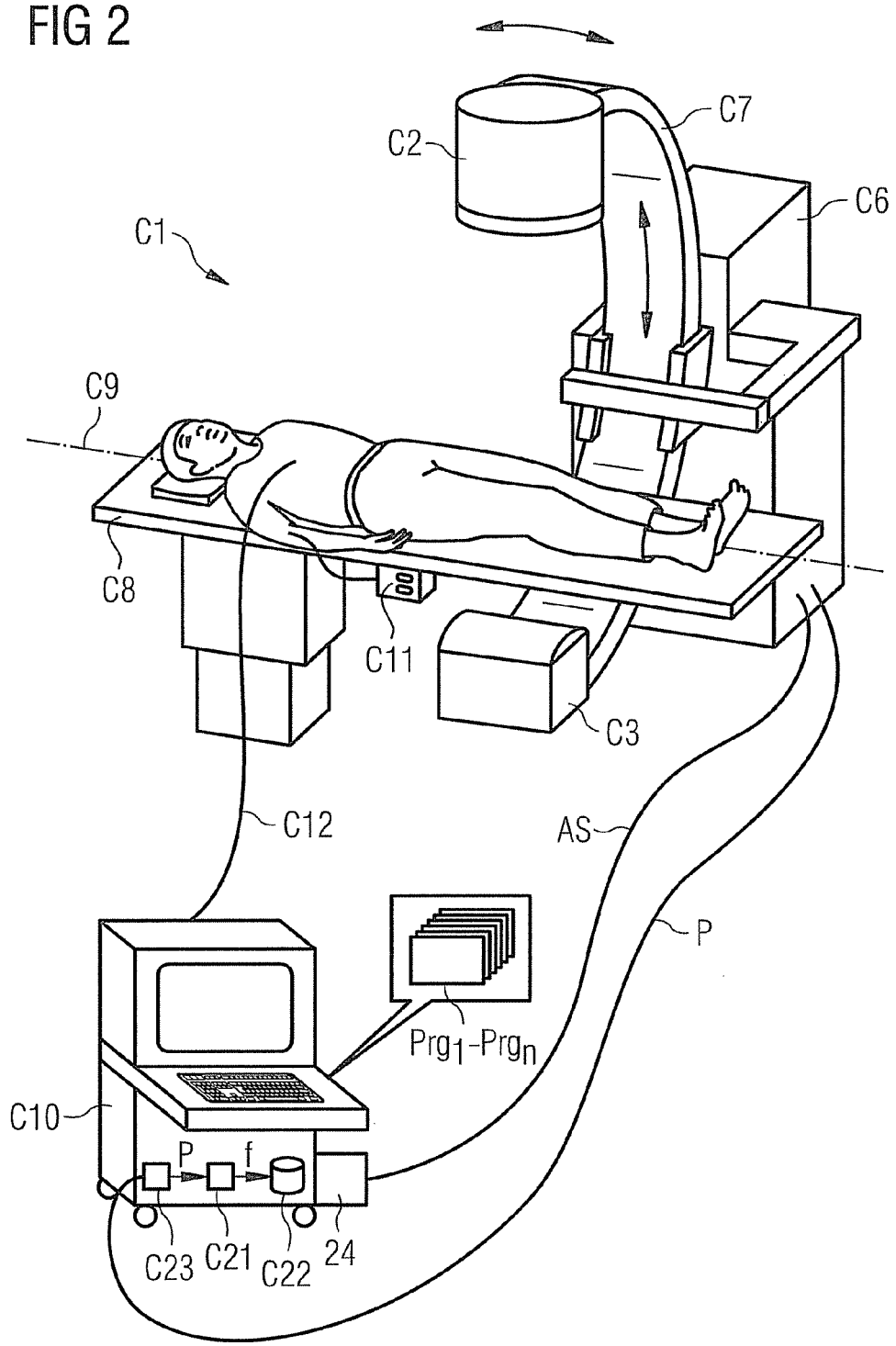
FIG. 2: a second diagrammatic illustration of an example embodiment of a computed tomography system with an image reconstruction component.

FIG. 2 shows a C-arm system, in which in contrast to the CT system in FIG. 1 the housing C6 supports the C-arm C7, to which firstly the x-ray tube C2 and secondly the opposing detector C3 are attached. The C-arm C7 is swiveled for scanning likewise about a system axis C9, so that scanning can take place from a plurality of scanning angles and corresponding projection data p can be determined from a plurality of projection angles. The C-arm system C1 in FIG. 2, like the CT system in FIG. 1, has a control and arithmetic unit C10 of the type described for FIG. 1.

Embodiments of the invention can be used in both of the systems shown in FIGS. 1 and 2. Furthermore, it can in principle also be employed for other CT systems, e.g. for CT systems with a detector forming a complete ring.

In the following it is described how CT images can be obtained by way of an iterative image reconstruction algorithm.

In conventional non-iterative image reconstruction methods so-called cone beam artifacts occur in the CT image, as do spiral artifacts. Cone beam artifacts arise because the individual layers, i.e. the different detector lines, are assumed during image reconstruction to lie in parallel to one another, whereas in reality they are slanted in respect of one another. This effect increases as the number of detector lines increases. Spiral artifacts in contrast stem from the data interpolation which in spiral scans is necessary in conventional reconstruction algorithms in order to have data present for all Z positions and rotation angles of the x-ray tube.

An advantage of iterative reconstruction methods compared to conventional non-iterative procedures, e.g. FBP (Filtered Backprojection), is that the cone beam artifacts and spiral artifacts described do not occur in a CT image which was iteratively reconstructed. Moreover, the image noise is also reduced compared to images reconstructed in the conventional way. These two positive effects are however achieved at different time points in the course of the iterative calculation: it is found that in iterative reconstruction the image artifacts are already eliminated after a few, e.g. two, iteration cycles, whereas a convergence of the image noise is not achieved until after further iteration cycles.

In an iterative reconstruction the measured data $p_{in}$ which typically is present in semi-parallel cone beam geometry, i.e. after azimuthal parallel rebinning, is used as an input signal. There then follows a reconstruction of initial image data $f_0$ from the projection measured data $p_{in}$ by means of the backprojection operator $Q^T$. To this end a convolution backprojection method is used, for example. From this initial image data $f_0$ a projector Q (a projection operator which should emulate the measurement process mathematically as closely as possible) is used to generate synthetic projection data $P_{syn}$. The difference between the synthetic projection data $p_{syn}$ and the measured data $p_{in}$ is then backprojected with the backprojection operator $Q^T$ adjoining the projector Q and in this way a residual or correction image $f_{corr}$ is reconstructed, with which the initial image $f_0$ is updated. As a result the image $f_1$ of the first iteration is obtained. This updated image data $f_1$ can in turn be used to generate new synthetic projection data $p_{syn}$ in a next iteration step with the aid of the projection operator Q, again to calculate the difference from the measured signals $p_{in}$ from this and to calculate a new residual image $f_{corr}$, with which again the image data $f_1$ for the current iteration stage is improved and thus the image data $f_2$ for the next iteration stage is obtained, etc.

In addition to this basic mechanism, in iterative image reconstructions a so-called regularization term is furthermore normally employed, which reduces the image noise and determines its behavior. In each iteration cycle the regularization term is also used in addition to the correction image $f_{corr}$, and effects a noise averaging and stabilization of the solution and thus a convergence of the iterative algorithm.

In an iterative reconstruction based on a filtered backprojection (FBP) the update equation for the three-dimensional image volume f is:

$$f_{k+1} = f_k + [\alpha \cdot Q^T \cdot K \cdot (Q \cdot f_k - p_{in}) - \gamma \cdot R(f_k)] \quad \text{Formula (1)}$$

Here, $f_{k+1}$ is the image of the k+1-th iteration which is calculated from the image $f_k$ of the k-th iteration.

The correction term—this corresponds to the correction image $f_{corr}$—is $\alpha \cdot Q^T \cdot K \cdot (Q \cdot f_k - p_{in})$. Here, α is a constant factor which determines the degree of the correction of the image $f_k$ by the correction image $f_{corr}$. A Ramlak kernel (linear ramp in the frequency space) is normally selected as kernel K. The correction term corrects image errors that are caused by the non-exact backprojector $Q^T$.

The correction term corresponds to a highpass filtering of the image $f_k$. For this reason the correction term effects an increase in the image noise. The regularization term counteracts this. Without the use of the regularization term the image noise would hence increase from iteration to iteration. The regularization term is $\gamma \cdot R(f_k)$, where γ represents a constant factor which determines the degree of the admixture of the regularization term. $R(f_k)$ is a non-linear highpass filter which is applied to the image $f_k$ of the k-th iteration stage. In the update equation the regularization term works like a non-linear lowpass because of the minus sign.

If formula (1) is examined, the correction term represents a component which contains a switch from the image data space to the measured data space. Because of the necessary forward and backward projection calculations this is compute-intensive and thus costly in terms of resources and time. In contrast, the regularization term represents a component which corresponds to a pure manipulation in the image data space, which requires less computing effort.

The function of the correction term is to eliminate image errors, whereas the regularization term effects a denoising of the image. As already mentioned, the aim of eliminating the image errors is generally achieved with significantly fewer iterations than the denoising of the image. However, each further iteration requires considerable computing effort, so that it would be advantageous to exit the iteration loop after eliminating the image errors.

Figure 3:
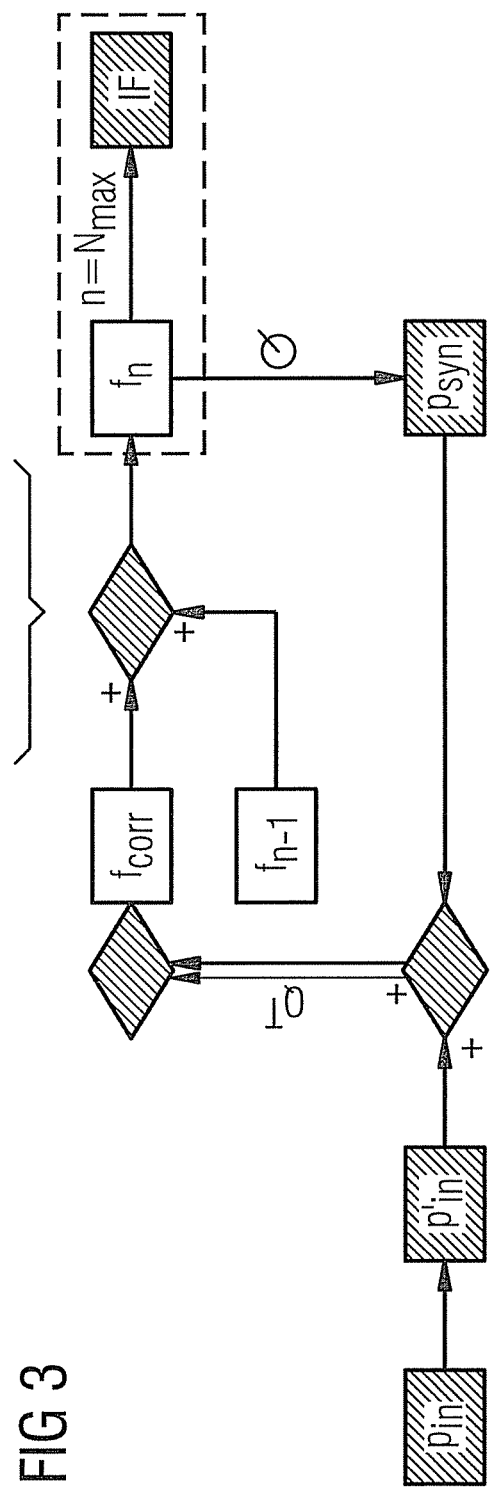
FIG. 3: a flow chart.

Hence as shown in FIG. 3 the iterative algorithm is applied without using the regularization term. It is thus employed as an update equation $$f_{k+1} = f_k + \alpha \cdot Q^T \cdot K \cdot (Q \cdot f_k - P'_{in}) \quad \text{Formula (2)}.$$

As explained above, the initial image $f_0$ is calculated from the measured data $p_{in}$. To calculate each correction image $f_{corr}$ use is made not of the measured data $p_{in}$ but of modified measured data $P'_{in}$ obtained therefrom, the function of which is explained in more detail below. At the point at which the curly bracket is drawn in, the regularization term according to formula (1) would normally be employed, but this is dispensed with according to formula (2).

Since the noise reduction is not brought about by the regularization term, a non-linear image filter IF is employed for noise reduction after the end of the iteration, i.e. if the number of iterations n has reached a particular maximum number $N_{max}$. Normally such image filters work satisfactorily only if the image processed by them has a particular grayscale characteristic or texture. It must therefore be ensured that the image which the iterative algorithm supplies according to formula (2) and FIG. 3 has a defined status in respect of the image noise. As already explained, the correction term increases the image noise from iteration to iteration because of its highpass effect, so that if the regularization term is simply omitted, no defined image noise of the result image can be effected by the iterative algorithm.

Hence the iterative algorithm according to formula (2) should be noise-neutral; this means that the noise increase is prevented by the correction term. This occurs because the measured values $p_{in}$ are filtered two-dimensionally according to formula (3). The measured values $p_{in}$ are present here in two-dimensional form for each projection angle, in accordance with the two-dimensional detector, which extends in the channel and line direction.

$$P'_{in} = ((Q \cdot Q^T)_{xy} \cdot I/K) x (Q \cdot Q^T)_z \cdot p_{in} \qquad \text{Formula (3)}$$

$(Q \cdot Q^T)_{xy}$ designates the transverse component, i.e. the proportion working in the channel direction or within the plane of a layer of the examination object, and $(Q \cdot Q^T)_z$ the axial component, i.e. the proportion of the three-dimensional operator $(Q \cdot Q^T)$ working in the line direction Z or perpendicular to the layer plane. This operator $(Q \cdot Q^T)$ essentially characterizes the interpolation functions in the forward projection and backprojection. The backprojection is typically voxel-driven, i.e. the detector signal assigned to a voxel must be determined by (e.g. linear) interpolation. Similarly during the projection of the image signal to calculate the line integral the image signals must be interpolated voxel by voxel (linearly). $(Q \cdot Q^T)_{xy}$ and $(Q \cdot Q^T)_z$ work as lowpass; they are both short-range filters.

The operator I is a CT convolution kernel that can be stipulated by the user, i.e. by the person evaluating the CT image, normally a radiologist. In the case of a filtered backprojection such a CT filter kernel is applied in the filter step; this determines the noise characteristic of the result ing image. In the case of the present iterative algorithm too, the CT filter kernel I determines the noise characteristic of the image output by the iterative algorithm. The expression I/K corresponds to the modulation transfer function of the CT image recording. In other words, in addition to the lowpass filtering explained above, the input signal is lowpass-filtered with the modulation transfer function of the input kernel I.

$P'_{in}$ is thus a lowpass-filtered version of the measured data $p_{in}$, with a particular frequency characteristic stipulated by the kernel I.

In the correction term the synthetic data $p_{syn}$ is not compared to the measured data $p_{in}$ according to formula (2), but to the modified measured data $P'_{in}$. Because of the nature of the modified measured data $P'_{in}$ this firstly means that no noise increase in the iteration image is added by the correction image $f_{corr}$, and secondly that after the last iteration the result image has the frequency characteristic or grayscale characteristic stipulated by the operator I. Thus through the use of the modified data $P'_{in}$ a dedicated and desired noise characteristic of the image present after the iteration is aborted is enforced.

By using a suitable filter IF after the end of the iterative reconstruction a desired definition-to-noise ratio of the image can be set. Non-linear three-dimensional image filters are suitable for this. It is advantageous to use a filter which firstly performs a smoothing of the image in homogeneous regions; this enables the noise power spectrum to be set and thus direct control of the desired noise texture. Secondly the filter can exempt non-homogeneous regions in which a significant structure is present in the image from smoothing, so that edges are recessed during smoothing. By using a suitable filter function it is even possible to reinforce the edges. Overall such a filter thus effects smoothing while preserving the edges. Such a filter can be applied either simply or iteratively to the image to be filtered.

A specific example of such a filter can be found in our own subsequently published application DE 10 2009 039 987.9, the entire contents of which are hereby incorporated herein by reference. A filter function is reproduced in formula (8) of this application. This can also be applied in simplified terms, in particular in that only the term designated by II, and not the term designated by I, is employed. Another specific example of such a filter, which in terms of contents corresponds as closely as possible to the first example, was given in a lecture at RSNA2009 in Chicago in the Physics session (CT: New Methods) on Nov. 29, 2009 from 11:15-11:25 by Dr. T. Flohr, the entire contents of which are hereby incorporated herein by reference.

The image $f_{IR-IF}$ present after processing by the filter IF can be output as a result image $f_{Final}$.

Alternatively it is possible to merge the filtered image $f_{IR-IF}$ with the image $f_{k_{max}}$ present after the iteration and before the filtering according to:

$$f_{Final} = \beta \cdot f_{k_{max}} + (1-\beta) \cdot f_{IR-IF} \qquad \text{Formula (4)}$$

Here $\beta$ is a parameter between 0 and 1. As a result, an optimization of the grayscale characteristic of the result image $f_{Final}$ can be achieved.

It has thus been shown that during an iterative reconstruction the regularization term can be done away with, as a result of which fewer iterations are necessary until convergence is reached. Instead of the regularization term which normally determines the noise characteristic of the result image, a suitable image filter is applied downstream of the iterative algorithm. This corresponds to a decoupling of correction term and regularization term during the iterative image reconstruction. In order to make a dedicated noise characteristic available for the input image of the image filter, the measured data undergoes a two-dimensional filtering using a filter kernel which stipulates this noise characteristic.

The invention was described above using an example embodiment. It should be understood that numerous changes and modifications are possible, without going beyond the framework of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for reconstructing image data of an examination object from measured data, wherein the measured data is captured during a relative rotary motion between a radiation source of a computed tomography (CT) system and the examination object, the method comprising:
   modifying the measured data to achieve a particular grayscale characteristic of the image data to be reconstructed; and
   calculating the image data by way of an iterative algorithm using the modified measured data, the iterative algorithm including a correction term for iteratively correcting image errors, wherein
   upon a termination of the iterative algorithm, the calculated image data undergoes a noise-reduction processing.

2. The method as claimed in claim 1, wherein the modifying the measured data is based on a CT convolution kernel, which stipulates the particular grayscale characteristic.

3. The method as claimed in claim 2, wherein the particular grayscale characteristic is adapted to the noise-reduction processing.

4. The method as claimed in claim 2, wherein the noise-reduction processing includes a non-linear filtering which smoothes the image data while preserving edges of the image data.

5. The method as claimed in claim 1, wherein the particular grayscale characteristic is adapted to the noise-reduction processing.

6. The method as claimed in claim 1, wherein the noise-reduction processing includes a non-linear filtering which smoothes the image data while preserving edges of the image data.

7. The method as claimed in claim 1, wherein, after the noise-reduction processing, the image data processed is merged with the unprocessed image data.

8. The method as claimed in claim 1, wherein the calculating the image data comprises:
   calculating first image data from the measured data, and
   calculating subsequent image data during subsequent iterations of the iterative algorithm using the modified measured data.

9. The method as claimed in claim 1, further comprising:
   calculating measured data during each iteration of the iterative algorithm from the calculated image data; and
   comparing the calculated measured data with the modified measured data.

10. The method as claimed in claim 9, wherein further comprising:
    calculating correction data is based on the comparing; and
    correcting the calculated image data based on the calculated correction data.

11. A non-transitory computer program comprising:
    program code configured to perform the method as claimed in claim 1 when the computer program is run on a computer.

12. A non-transitory computer readable medium including a computer program product, the computer program product comprising computer instructions, which when executed by a processor, causes the processor to perform the method of claim 1.

13. The method as claimed in claim 1, wherein the iterative algorithm further includes a regularization term which is not used during the iteratively correcting image errors.

14. The method as claimed in claim 13, wherein the iterative algorithm is based on a decoupling of the correction term and the regularization term.

15. The method as claimed in claim 14, wherein the decoupling results in a faster convergence of the iterative algorithm compared to a reconstruction method based on an iterative algorithm with a coupled correction and regularization terms.

16. A control and arithmetic unit for reconstructing image data of an examination object from measured data of a computer tomography (CT) system, the control and arithmetic unit comprising:
- a program memory configured to store program code, the program code, when executed, performing functions including:
- modifying the measured data to achieve a particular grayscale characteristic of the image data to be reconstructed; and
- calculating the image data by way of an iterative algorithm using the modified measured data, the iterative algorithm including a correction term for iteratively correcting image errors, wherein
- upon a termination of the iterative algorithm, the calculated image data undergoes a noise-reduction processing.

17. A CT system comprising:
a control and arithmetic unit as claimed in claim 16.

* * * * *